(12) United States Patent
Leonhardt et al.

(10) Patent No.: US 8,679,463 B2
(45) Date of Patent: Mar. 25, 2014

(54) ORAL HYGIENE PRODUCTS AND METHOD

(75) Inventors: Charles Leonhardt, Huntington, NY (US); John Busby, Huntington, NY (US)

(73) Assignee: Dentech, Inc., Huntington, NY (US)

( * ) Notice: Subject to any disclaimer, the term of this patent is extended or adjusted under 35 U.S.C. 154(b) by 0 days.

(21) Appl. No.: 13/385,420

(22) Filed: Feb. 17, 2012

(65) Prior Publication Data

US 2013/0064778 A1    Mar. 14, 2013

Related U.S. Application Data

(63) Continuation of application No. 11/365,167, filed on Mar. 1, 2006, now Pat. No. 8,163,271.

(51) Int. Cl.
| | |
|---|---|
| *A61Q 11/00* | (2006.01) |
| *A61K 8/00* | (2006.01) |
| *A61K 8/02* | (2006.01) |
| *A61K 8/21* | (2006.01) |
| *A61K 8/24* | (2006.01) |
| *A61K 8/27* | (2006.01) |
| *A61K 8/36* | (2006.01) |

(52) U.S. Cl.
USPC .................. 424/49; 424/52; 424/55; 424/57; 424/401

(58) Field of Classification Search
USPC .................. 424/49, 52, 55, 57, 401
See application file for complete search history.

(56) References Cited

U.S. PATENT DOCUMENTS

2004/0086467 A1 * 5/2004 Curro .............................. 424/52
2004/0126335 A1 * 7/2004 Faller et al. ..................... 424/52

FOREIGN PATENT DOCUMENTS

| HU | 67731 | * | 4/1995 |
| JP | 411043424 | * | 2/1999 |
| WO | WO 99/20237 | * | 4/1999 |

* cited by examiner

*Primary Examiner* — Lezah Roberts
(74) *Attorney, Agent, or Firm* — Stephen E. Feldman; Feldman Law Group, P.C.

(57) ABSTRACT

The present invention is directed towards a composition for highly efficient and quick plaque and tartar removal and inhibition including pure ascorbic acid crystals and/or granulars (vitamin C) and an enamel repairing composition such as hydroxyapatite. The composition can contain from about 10% up to 90% of ascorbic acid without compromising the tooth enamel because hydroxyapatite will repair any damage to the enamel. The composition can be used as dental powder, toothpaste, mouthwash, mouth spray and chewing gum in order to cover a wide range of consumers in different settings.

5 Claims, No Drawings

ORAL HYGIENE PRODUCTS AND METHOD

This is a continuation of U.S. patent application Ser. No. 11/365,167.

FIELD OF THE INVENTION

The invention relates to compositions and methods useful in promoting oral health and hygiene.

BACKGROUND OF THE INVENTION

Tooth decay and gum inflammation are related to the activity of microbial plaque, which consists of bacterial products, leukocytes, epithelial cells and saliva components. In the presence of saliva, proliferating bacteria attach to places with retained food such as gum line, tongue, tooth spacing, pits and fissures. The bacteria decompose retained food, releasing toxic substances and forming plaque and tartar (an advanced formation of plaque). This results in bad breath, gum inflammation and dental caries.

The majority of oral care products are artificial and harmful when ingested. Some of them induce allergic reactions and others are even carcinogenic when presented in high dosages. Antibiotics have also been used to fight plaque formation. However, antibiotic applications usually result in the development of resistant microorganisms. As a consequence, there is a trend toward the use of safe ingredients in oral care products. Also, the emphasis in oral hygiene has been placed on chemical methods of removing plaque and tartar. These chemical methods eliminate the need for the mechanical action of scrapers.

The present invention relates to a safe oral composition, which chemically removes plaque and tartar. Moreover, it inhibits further plaque accumulation and tartar information. Thus, the invention is highly efficient in plaque and tartar removal and inhibition. The invention is also a natural teeth whitener and a preservative.

DESCRIPTION OF RELATED ART

Oral care products containing safe ingredients, such as baking soda, are well known. However, high concentration of baking soda required to provide adequate cleaning is abrasive and distasteful.

Saponin is another type of safe plaque cleanser, which produces foaming and cleans without the use of artificial surfactants. However, saponins are of plant origin (Quillaja and/or Yucca tree) and have to be extracted from plants, which is a laborious and time consuming process.

Ascorbic acid (vitamin C) is a safe ingredient and has been used in oral compositions. However, those compositions usually contain small amount of ascorbic acid and mainly rely on other cleaning ingredients. Other compositions use ascorbic acid but fail to efficiently utilize its strong and safe cleaning capacity heavily relying on catalysts for auto-oxidation, such as copper, and the synergetic action of other cleaning agents. None of the above prior art describes, suggests or renders obvious the enormous cleaning capacity of pure ascorbic acid crystals and/or granulars unaided by other cleaning agents.

SUMMARY OF THE INVENTION

While the prior art avoids using high concentrations of ascorbic acid as harmful to the tooth enamel, the preferred embodiment of the present invention can contain from about 10 up to 90% of ascorbic acid since hydroxyapatite will efficiently repair and protect the enamel. Also, while the prior art compositions require treatment longer than one minute, the preferred embodiment of the present invention requires only a 30 second treatment.

Again, the present invention is directed to an oral composition for plaque and tartar removal and control. The composition contains pure crystals and/or granulars of ascorbic acid (vitamin C) and hydroxyapatite. When used in high concentrations (from 10% up to about 90%), ascorbic acid is highly efficient in quickly dissolving and detaching plaque and tartar upon contact. Such high concentrations will not compromise the tooth enamel because hydroxyapatite will repair and protect it. In one exemplary embodiment, any irritation, such as, oral mucosa that may be caused by the ascorbic acid can be prevented by using some form of menthol in composition.

The invention chemically dissolves plaque and tartar in usually less than 60 second. It eliminates the need for additional cleaning agents and the mechanical action of scrapers. Furthermore, the invention is highly efficient in inhibiting plaque accumulation and tartar formation if used consistently.

The most efficient form of the present inventions is the dental powder containing from 10% up to 90% of ascorbic acid crystals and/or granulars. However, the invention can be used in a liquid form as aqueous and alcohol aqueous solutions containing about 10-40% of ascorbic acid. The invention can contain additional ingredients such as sweeteners, flavoring and coloring agents, and can be used in a used in a variety of commercial products such as toothpaste, chewing gum, mouthwash with and without alcohol and mouth spray in order to cover a wide range of consumers in different settings.

DETAILED DESCRIPTION OF THE INVENTION

It is an object of the present invention to provide improved plaque and tartar removal and control. The invention is based on the enormous cleaning capacity of pure ascorbic acid crystals, granulars and/or any other form of pure ascorbic acid unaided by additional cleaning ingredients. Please note, a grandular form of ascorbic acid may be used instead of the crystalline form.

The present invention uses high concentrations of ascorbic acid where hydroxyapatite is used to repair and protect the tooth enamel. It is worthy to note, that ascorbic acid is the preferred compound of the present invention but any acidic compound that incorporates high cleaning efficacy may be used as a substitute for the ascorbic acid.

Ascorbic acid (vitamin C) is a non-toxic compound, which is harmless when ingested. It has been known that vitamin C deficiency causes scurvy when collagen formation is compromised. In addition, a diet deficient in vitamin C renders gingiva more susceptible to bacterial attacks. Thus, ascorbic acid is not only harmless but also important for the human organism's healthy functioning. Therefore, it is one of the objects of the present invention to provide a safe oral hygiene composition, which promotes human health.

The harmless nature of the present invention makes it even more suitable for use by children. Since many parents are not able to efficiently control their children's oral hygiene, the present invention solves this problem by providing a safe, healthy and efficient cleaning procedure eliminating the need for long and extensive brushing.

Different studies have confirmed the role of microbial plaque as a major factor in dental caries and periodontal diseases. The most common types of periodontal disease are gingivitis and periodontitis. Gingivitis is an early stage gum disease characterized by gum inflammation, swelling and bleeding. Periodontitis is a late stage gum disease, in which tooth supporting bone is slowly lost. In view of plaque's major role in dental diseases, one of the objects of the present invention is to provide safe and effective oral hygiene composition for combating bacteria associated with dental plaque, caries, and periodontal diseases.

Pure ascorbic acid crystals and/or granulars (more than 70% purity) in the form of dental powder can be viewed as the most efficient embodiment of the invention. The size of the crystals and/or granulars can be but is not limited to 5 u-50 u. When used in high concentrations (ranging from over 10% to about 90%), the ascorbic acid crystals and/or granulars have enormous cleaning capacity eliminating the need for other cleaning agents and further mechanical cleaning. Such high concentrations are extremely effective in killing a wide spectrum of bacteria comprising the oral microflora: *Actinomyces viscosus,* alpha *Streptococcus, Candida albicans, Escherichia coli, Pseudomonas aeruginosa, Staphylococcus epidermidis* and *Streptococcus* mutants.

The present invention does not compromise the tooth enamel even in the presence of 90% or more of ascorbic acid since the hydroxyapatite will protect and repair the enamel. The invention can contain from 0.2% up to about 1.0% of hydroxyapatite but the preferred amount is 0.46% by weight.

Hydroxyapatite is the major component, and an essential ingredient, of normal bone and teeth. It is a thermally unstable compound, decomposing at temperature from about 800-1200° C. depending on its stoichiometry. Hydroxyapatite supports bone ingrowth and osseointegration when used in orthopaedic, dental and maxillofacial applications.

Hydroxyapatite adheres to the surfaces of teeth and promotes their recalcification and strengthening. It has been successfully used in a dental fine filling method for protecting and restoring pits, fissures and lesions in enamel. Also, hydroxyapatite absorbs dental plaque causing tooth decay. Studies have showed the absorption of oral Streptococci to hydroxyapatite.

In addition to ascorbic acid and hydroxyapatite, the dental powder form of the present invention contains about 10-20% tricalcium phosphate, 0.1-0.2% menthol and 4-6% zinc citrate. Tricalcium phosphate is used as a filler and carrier for the ascorbic acid crystals, menthol is a local anesthetic and counterirritant, and zinc citrate is an agent preventing plaque adherence to the tooth enamel. The dental powder can also contain fluoride (especially in regions where water has insufficient amount of fluoride), sweeteners, flavoring and coloring agents.

Ascorbic acid is also a natural whitener, eliminating the need for additional whitening agents. However, the dental powder can contain additional whitening ingredients such as sodium carbonate peroxidase (about 3-5%) and hydrated silica (about 5-7%).

The ascorbic acid crystals and/or granulars can also be included in water-free pastes such as a water-free glycerol paste, chewing gums, aqueous and alcohol aqueous solutions. The aqueous solutions can contain up to 80% water and the alcohol solutions can contain up to 30% denatured alcohol and up to 50% water. The alcohol solutions can contain thymol, menthol or other alcohols.

It is important to note that ascorbic acid is a preservative and its solutions need not be specially stored or packaged in sealed containers. Given invention's preserving characteristics, its solutions can be made with tap water without compromising the solutions' cleaning properties. However, purified water is preferred. Also, the invention can use additional preservatives such as sodium benzoate in an amount of about 0.2-0.4%.

The present invention can contain other ingredients including sweeteners, flavoring and coloring agents could be added to achieve different tastes and flavors.

Suitable sweeteners are sodium saccharine, aspartame, cyclamates, sucrose, sorbitol, mannitol, and maltitol. The preferred sweeteners, however, are sodium saccharine (0.01-0.02%). Suitable flavoring agents are natural and synthetic oils. The preferred flavoring is a combination of spearmint and peppermint in an amount of about 0.2-0.4%. However, the invention can contain other flavoring agents such as cinnamon oil, wintergreen oil, bay oil, citrus oil, lemon oil, lime oil clove oil and menthol.

The invention can also contain medications or bioactive ingredients such as antifungal, anti-inflammatory, antibiotic, anti-bacterial, analgesic and immunosuppressive agents.

The dental powder form of the present invention becomes liquid upon contact with saliva and chemically dissolves and detaches plaque from teeth, gum and tongue in about 15 to 90 seconds. Furthermore, the formed liquid quickly breaks the barrier between the teeth and calcified tartar.

Similarly, the solution forms of the invention react with plaque and form a fatty like substance, which detaches and washes plaque and tartar away from teeth, gum and tongue. This eliminates the need for mechanical scrapers, and their maintenance and storage. The solutions can also remove plaque between teeth depending on the strength of the rinse which provides access to the narrowest places. The amount of crystals and/or granulars in those solutions can be varied in order to comfortably achieve the desired taste and effectiveness.

Thus, one of the improved functions of the present invention is the fast and efficient plaque removal and inhibition. Plaque is a fatty substance consisting of bacterial colonies surrounded by gel-like intercellular substance derived chiefly from the bacteria themselves. Plaque also contains saliva, epithelial cells and leukocytes. It usually accumulates on tooth surface, gum, gum line and tongue resulting in bad breath, gum disorders and caries. Bacterial colonies of the plaque use dietary carbohydrates as a source of energy producing acids. The acids demineralize tooth enamel and dentine attacking gum tissue and reacting with the calcium in the teeth.

Persons brushing their teeth normally take approximately 1 minute limiting exposure time to either chemical or mechanical action. Most dentists and oral hygienists recommend longer treatments for efficient plaque removal. However, the invention acts quickly chemically dissolving plaque and tartar, and leaving smooth tooth surface, clean gum and tongue in less than 15 to 90 seconds. Furthermore, ascorbic acid softens plaque formed between teeth and loose gum. Plaque accumulation is inhibited resulting in tighten gum line, fresh breath and refreshing mouth taste. As a consequence, dental caries and periodontal diseases are effectively prevented:

Another improved function of the present invention is the fast and efficient tartar removal and inhibition. Tarter constitutes an advanced formation of plaque. Tarter is formed when inorganic salts and phosphate in saliva, deposit on plaque. This leads to calcification and a hard surface formation, which is difficult to remove. Leaving tartar for longer time periods may result in serious tooth and gum disorders. Tarter is usually removed by mechanical means such as ultrasonic scrapers, picks and brushes. However, ascorbic acid tends to break down the barrier between the teeth and calcified tartar.

Thus, each application of the invention shrinks and inhibits tartar formation resulting in the prevention of dental caries and periodontal diseases.

The present invention can be used in a variety of commercial product forms, such as mouthwash, mouth spray, toothpaste, dental powder and chewing gum in order to cover a wide range of consumers in different settings. While mouthwash and toothpaste and dental powder are more suitable for domestic use, mouth spray and chewing gum can be universally applied.

The toothpaste and dental powder form of the invention are more suitable for use in domestic settings, where they are applied to teeth with or without a brush. After toothpaste application and brushing is completed, the toothpaste and dental powder are rinsed with water and expectorated. Similarly, the mouthwash form of the present invention can be comfortably used in domestic settings, where a person has the opportunity to extensively rinse his or her oral cavity. After the rinse is completed, the mouthwash is usually expectorated and the oral cavity is rinsed with water. It is important to note that any accidental swallowing will not be harmful given the ascorbic acid's safe nature.

In contrast to the mouthwash and toothpaste forms, which are more suitable for domestic use, the mouth spray and chewing gum forms of the invention can be universally used. Although many people are willing to take oral hygiene measures throughout the day, they find those measures to be inconvenient, and sometimes awkward. For example, they may not have constant access to a bathroom or a sink feeling unable to use toothpastes and mouthwashes. Also, they may be uncomfortable being seen carrying around items such as a toothbrush, a toothpaste or a bottle of mouthwash.

Consequently, there is a great need for oral hygiene products which are convenient, portable and swallowable. Such products are the mouth spray and gum forms of the present invention.

Mouth spray requires spraying the solution into the oral cavity and retaining it for about 15 to 90 seconds to allow efficient plaque and tartar removal. After that the solution could be safely swallowed or simply expectorated. Mouth sprays could be packaged in portable bottles in order to fit pockets, purses and bags.

Chewing the gum form of the present invention is another form of universal application. Plaque and tartar can be dissolved and dislodged by chewing the gum for a short time period sufficient to remove plaque and tartar. Furthermore, a person can continue chewing the gum even after plaque is removed in order to inhibit plaque accumulation and tartar formation for longer time periods.

Below are example compositions using the preferred embodiments of the present invention.

EXAMPLE 1

The first example is a medicated chewing gum containing:
69.0% macticatory gum core
20.0% ascorbic acid crystals and/or granulars;
0.1% sodium saccharine;
0.5% hydroxyapatite;
0.2% spearmintlpeppermiilt flavor;
0.24% sodium fluoride;
0.001% blue #1;
5.0% zinc citrate trihydrate;
2.0% sucralose;
1.0% polymer coating for sugar-free chiclets;
0.1% sodium benzoate;
1.0% titanium dioxide;
0.859% other ingredients.

EXAMPLE 2

The second example is a tooth powder containing:
70.0% ascorbic acid crystals and/or granulars;
12.0% tricalciumphosphate or dicalciumphosphate;
0.1% menthol natural crystalline powder;
0.2% spearmint/peppermint flavor;
0.24% sodium fluoride;
3.0% sodium carbonate peroxide;
5.0% hydrated silica;
5.0% zinc citrate trihydrate;
2.0% sucralose;
0.5% hydroxyapatite;
1.0% titanium dioxide;
0.96% other ingredients.

EXAMPLE 4

The fourth example is a mouthwash with alcohol as deionized water containing:
20.0% ascorbic acid crystals and/or granulars;
10.0% sorbital solution;
0.01% sodium saccharine;
0.2% sodium benzoate;
0.2% spearmint/peppermint flavor;
0.0001% blue #1;
5.0% zinc citrate;
0.5% hydroxyapatite;
10.0% glycerin;
0.1% paloxamer 407;
0.24% sodium fluoride;
0.1% menthol in denatured alcohol;
0.1% thymol in denatured alcohol;
20.0% denatured alcohol with menthol and thymol;
33% deionized water;
0.5499% other ingredients.

EXAMPLE 5

The fifth example is a toothpaste containing:
34.0% ascorbic acid crystals and/or granulars;
10.0% sorbital powder;
0.5% hydroyapatite crystals;
0.01% sodium saccharine;
0.2% sodium benzoate;
0.2% spearmint/peppermint flavor;
5.0% zinc citrate trihydrate;
30.0% glycerin anhydrous;
0.24% sodium fluoride;
3.0% calcium orthophates;
5.0% hydrated silica;
10.0% tricalcuim phosphate;
1.0% sodium lauryl sulfate;
0.85% other ingredients.

Although the embodiments of the present disclosure have been described with specific examples, it is to be understood that the disclosure is not limited to those specific examples and that various other changes, combinations and modifications will be apparent to one of ordinary skill in the art without departing from the scope and spirit of the invention which is to be determined with reference to the following claims.

The invention claimed is:

1. A plaque and tarter removal and prevention dental toothpaste with enamel strengthening, repairing and protecting qualities for oral hygiene comprising:

a high concentration of ascorbic acid for plaque and tarter removal, at least 34% ascorbic acid;

a blend of hydroxyapatite crystals and sodium fluoride sufficient to strengthen tooth enamel, protect the tooth enamel against acid damage and repair fissures in the enamel in which plaque causing bacteria collect, the blend containing between 0.2-0.5% hydroxyapatite crystals and about 0.24% sodium fluoride;

an amount of zinc citrate trihydrate sufficient to prevent plaque adherence to the tooth enamel; and an amount of glycerin anhydrous.

2. The plaque and tarter removal and prevention dental toothpaste of claim 1 wherein combining a sufficient quantity of the plaque and tarter removal and prevention substance with saliva in a mouth forms a liquid that chemically dissolves and detaches plaque from teeth, gum and tongue and quickly breaks a barrier between the teeth and calcified tarter.

3. The plaque and tarter removal and prevention dental toothpaste of claim 1 further comprising:

an amount of tricalcium phosphate as a carrier for the ascorbic acid, the amount being between 10-20% tricalcium phosphate.

4. The plaque and tarter removal and prevention dental toothpaste of claim 3 further comprising:

an amount of hydrated silica sufficient as a whitener, the amount being between 5-7% hydrated silica.

5. The plaque and tarter removal and prevention dental toothpaste of claim 4 further comprising:

an amount of sodium saccharine sufficient as a sweetener, the amount being between 0.1-0.2% sodium saccharine.

* * * * *